US012721526B2

(12) United States Patent
Sayama

(10) Patent No.: US 12,721,526 B2
(45) Date of Patent: Sep. 1, 2026

(54) CARIES DETECTION DEVICE

(71) Applicant: TAMRON CO., LTD., Saitama (JP)

(72) Inventor: Atsushi Sayama, Saitama (JP)

(73) Assignee: TAMRON CO., LTD., Saitama (JP)

( * ) Notice: Subject to any disclaimer, the term of this patent is extended or adjusted under 35 U.S.C. 154(b) by 451 days.

(21) Appl. No.: 18/074,093

(22) Filed: Dec. 2, 2022

(65) Prior Publication Data

US 2023/0200660 A1 Jun. 29, 2023

(30) Foreign Application Priority Data

Dec. 28, 2021 (JP) ................................ 2021-214409

(51) Int. Cl.
*A61B 5/00* (2006.01)
*G01N 21/65* (2006.01)
*G06T 7/00* (2017.01)

(52) U.S. Cl.
CPC ........... *A61B 5/0088* (2013.01); *G01N 21/65* (2013.01)

(58) Field of Classification Search
None
See application file for complete search history.

(56) References Cited

U.S. PATENT DOCUMENTS

2005/0283058 A1* 12/2005 Choo-Smith ........ A61B 5/0088 356/73
2008/0063998 A1* 3/2008 Liang ................ G01B 11/2441 433/29
2008/0090198 A1* 4/2008 Liang .................. G01J 3/4406 433/29
2012/0013722 A1* 1/2012 Wong ................ G01B 11/2441 348/66
2012/0188538 A1* 7/2012 Patil ..................... G01N 21/65 356/479
2014/0146142 A1* 5/2014 Duret .................... A61C 19/04 348/46
2018/0146857 A1 5/2018 González Fernández et al.
2019/0117078 A1* 4/2019 Sharma .................... A61B 1/24
2019/0369025 A1* 12/2019 Yang .................... A61B 5/4547
2021/0169335 A1 6/2021 Ashida et al.

FOREIGN PATENT DOCUMENTS

JP 2015-078978 A 4/2015
JP 2018-521701 A 8/2018
WO WO 2019/106819 A1 6/2019

* cited by examiner

*Primary Examiner* — Baisakhi Roy
(74) *Attorney, Agent, or Firm* — Paratus Law Group, PLLC

(57) ABSTRACT

A caries detection device includes: a screening optical system that irradiates a tooth with a near-infrared ray from a light source to detect transmitted light through the tooth; and a Raman scattered light detection optical system that irradiates a caries candidate area of the tooth detected from information of the transmitted light with a near-infrared ray from the light source to detect Raman scattered light generated from the caries candidate area.

13 Claims, 7 Drawing Sheets

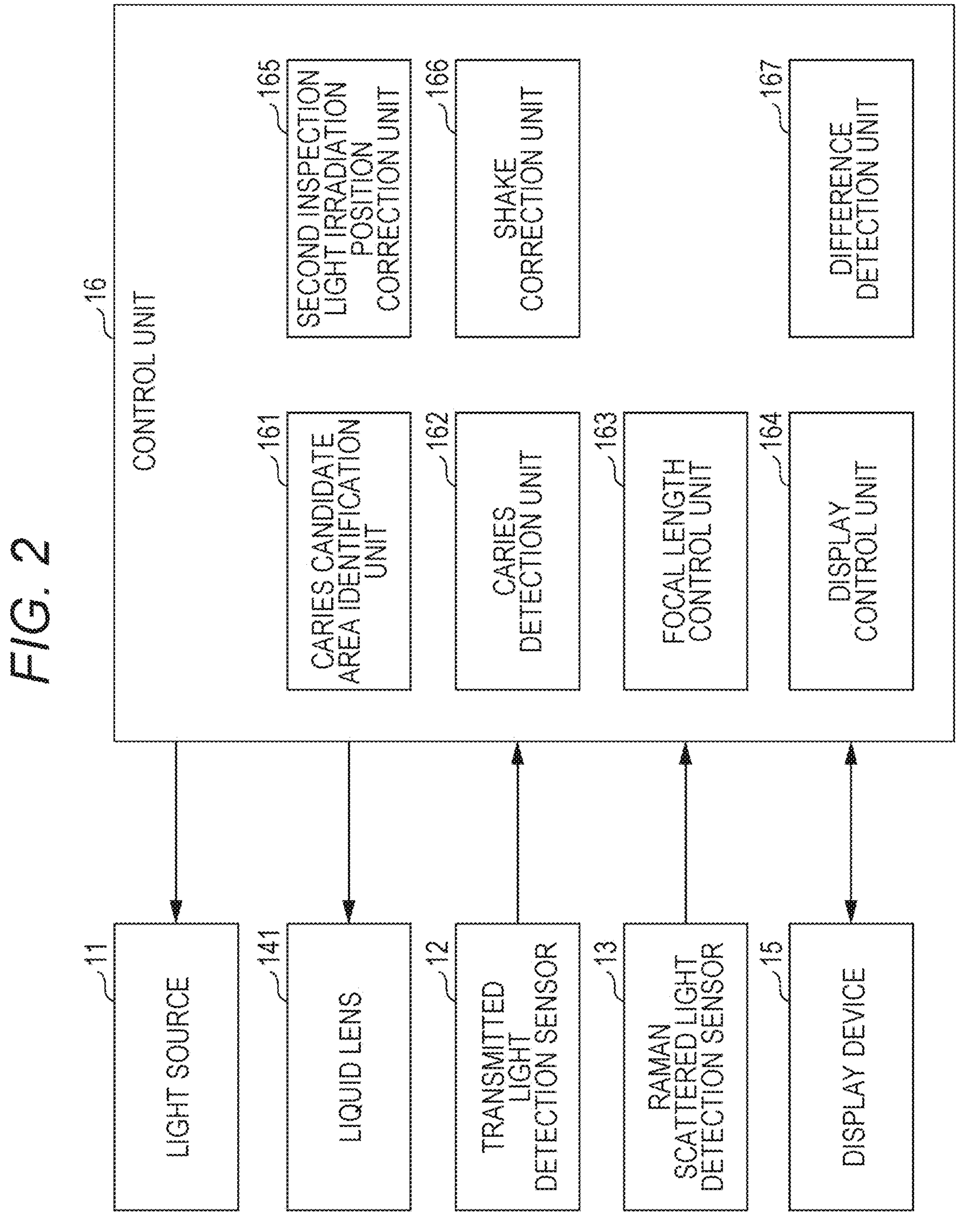
FIG. 2
16
CONTROL UNIT
161
CARIES CANDIDATE AREA IDENTIFICATION UNIT
162
CARIES DETECTION UNIT
163
FOCAL LENGTH CONTROL UNIT
164
DISPLAY CONTROL UNIT
165
SECOND INSPECTION LIGHT IRRADIATION POSITION CORRECTION UNIT
166
SHAKE CORRECTION UNIT
167
DIFFERENCE DETECTION UNIT
11
LIGHT SOURCE
141
LIQUID LENS
12
TRANSMITTED LIGHT DETECTION SENSOR
13
RAMAN SCATTERED LIGHT DETECTION SENSOR
15
DISPLAY DEVICE

FIG. 3

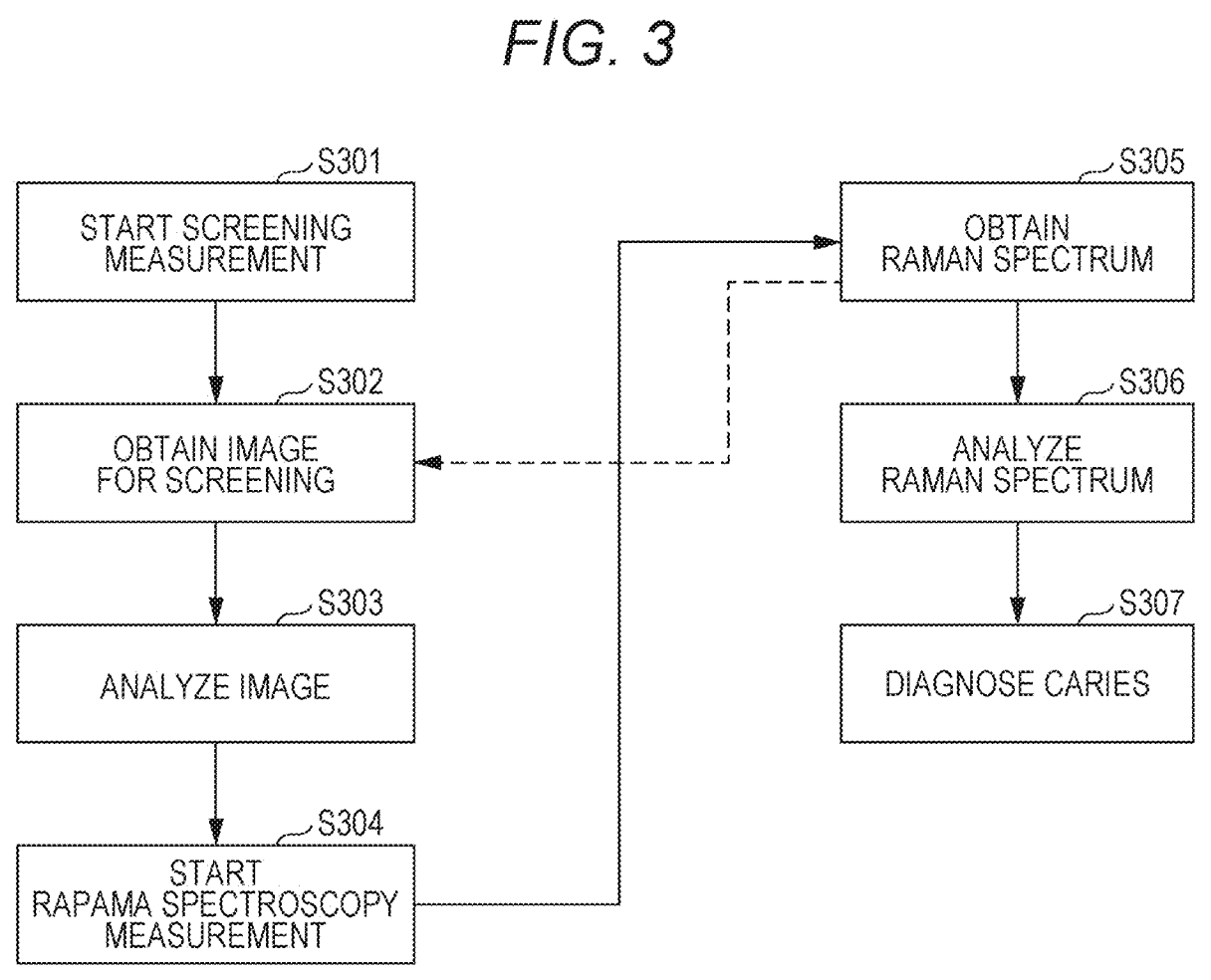

S301 START SCREENING MEASUREMENT

S302 OBTAIN IMAGE FOR SCREENING

S303 ANALYZE IMAGE

S304 START RAPAMA SPECTROSCOPY MEASUREMENT

S305 OBTAIN RAMAN SPECTRUM

S306 ANALYZE RAMAN SPECTRUM

S307 DIAGNOSE CARIES 2
20B
13
22
20A
243
FLUORESCENCE
21
241
24
INSPECTION LIGHT
RAMAN SCATTERED LIGHT
15
242
T

CARIES DETECTION DEVICE

CROSS-REFERENCE TO RELATED APPLICATIONS

This application is based on and claims the benefit of priority from Japanese Patent Application No. 2021-214409, filed on Dec. 28, 2021, the entire contents of which are incorporated herein by reference.

BACKGROUND OF THE INVENTION

Technical Field

The present invention relates to a caries detection device.

Related Art

It is known that periodontal diseases, such as "caries" and "periodontitis", account for a large proportion as a factor of losing tooth. Focusing on "caries", which is one of the periodontal diseases, Raman spectroscopy, which is one of spectroscopic techniques, is known (see, for example, JP 2015-78978 A, WO 2019/106819, and JP 2018-521701 A) as a technique of quantitatively evaluating the degree of progression of "caries".

SUMMARY OF THE INVENTION

In the Raman spectroscopy, however, the intensity of Raman scattered light is generally weak. Thus, it is necessary for quantitative evaluation to lengthen an integration time in order to obtain a sufficient signal intensity. This problem leads to an increase in time required for diagnosis, and a patient continues to keep his/her mouth open for a long period of time, which is very stressful for the patient. As described above, the conventional caries detection technique based on Raman spectroscopy has room for consideration from the viewpoint of shortening the time required for caries detection.

An object of one aspect of the invention is to achieve a technique capable of implementing caries detection by detection of Raman scattered light in a short period of time.

In order to solve the above problem, a caries detection device according to an aspect of the invention includes: a screening optical system that irradiates a tooth with first inspection light from a light source and detects transmitted light through the tooth or fluorescence generated from the tooth; and a Raman scattered light detection optical system that irradiates a caries candidate area, which is identified from information of the transmitted light or the fluorescence detected by the screening optical system, in the tooth with second inspection light from the light source and detects Raman scattered light generated from the caries candidate area.

According to one aspect of the invention, the caries detection by the detection of the Raman scattered light can be implemented in a short period of time.

BRIEF DESCRIPTION OF THE DRAWINGS

FIG. 2 is a block diagram illustrating an example of a functional configuration of the caries detection device according to the first embodiment of the invention;

FIG. 3 is a flowchart illustrating an example of a caries detection process according to the first embodiment of the invention;

DESCRIPTION OF THE EMBODIMENTS

First Embodiment

Hereinafter, an embodiment of the invention will be described in detail. A caries detection device according to the embodiment of the invention acquires an image of transmitted light through a tooth, which is an object to be measured, or an image of fluorescence emitted from the tooth by irradiation of inspection light to identify an area suspected of having caries. Further, the caries detection device irradiates the area suspected of having the caries with the inspection light to detect Raman scattered light emitted from the area. The following embodiment of the invention includes a system that drives the caries detection device.

Configuration of Device

Figure 1:
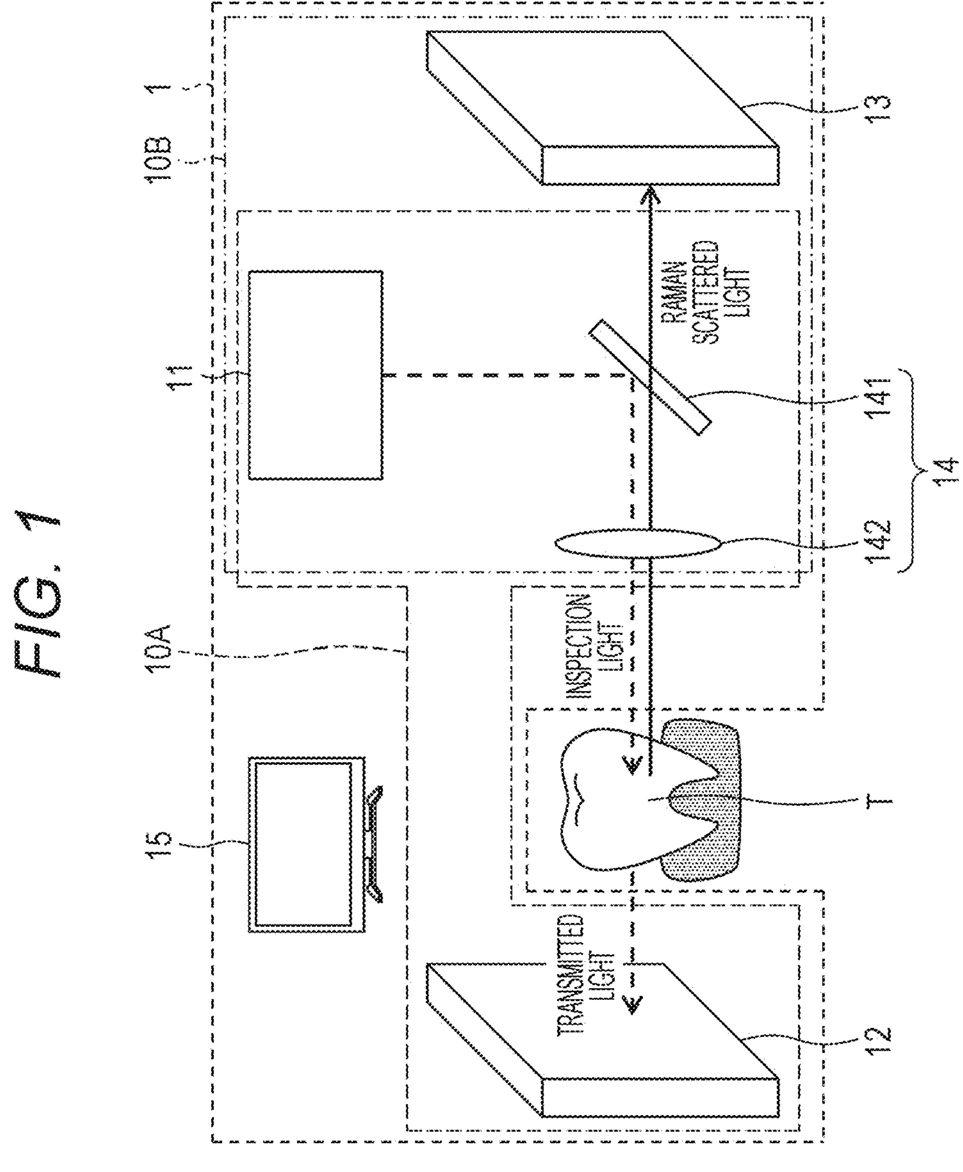
FIG. 1 is a diagram schematically illustrating a configuration of a caries detection device according to a first embodiment of the invention.

FIG. 1 is a diagram schematically illustrating a configuration of a caries detection device according to a first embodiment of the invention. As illustrated in FIG. 1, the caries detection device 1 includes a light source 11, a transmitted light detection sensor 12, a Raman scattered light detection sensor 13, an optical system 14, and a display device 15. In addition, the caries detection device 1 includes a control unit configured to control the operation of each unit.

The light source 11 is a light source that generates inspection light in a near-infrared region. As the light source 11, a high-output light source, such as a semiconductor laser and a fiber laser, can be used.

The transmitted light detection sensor 12 is a sensor configured to detect transmitted light through a tooth T, which is an object to be measured, irradiated with near-infrared rays. In the embodiment, the transmitted light is light transmitted through the tooth T among the near-infrared rays with which the tooth T is being irradiated. As the transmitted light detection sensor 12, an image sensor, such as a complementary metal oxide semiconductor (CMOS) camera and a charge-coupled device (CCD) camera, can be used, and the CMOS camera, for example, is used in the embodiment.

The Raman scattered light detection sensor 13 is a sensor configured to detect Raman scattered light generated from the tooth T irradiated with the near-infrared rays. As the Raman scattered light detection sensor 13, an optical detection element, such as a photodiode and a photomultiplier tube, can be used, and the photodiode, for example, is used in the embodiment.

The optical system 14 is configured to form a path of the inspection light and the transmitted light from the light source 11 to the transmitted light detection sensor 12, and is configured to form a path of the inspection light and the Raman scattered light from the light source 11 to the Raman scattered light detection sensor 13. The optical system 14 can be configured by a combination of optical elements. The optical system 14 can include an optical filter 141 and a variable focal length lens 142.

The optical filter 141 is an optical element that reflects the near-infrared rays from the light source 11 toward the tooth T and transmits the Raman scattered light from the tooth T. As the optical filter 141, an optical filter that reflects or transmits light of a specific wavelength, such as a band-pass filter, an edge filter, a long-pass filter, or a notch filter, can be used. In the embodiment, the optical filter 141 is, for example, the notch filter, the edge filter, or the long-pass filter.

The variable focal length lens 142 is an optical element that is disposed closer to the tooth T than the optical filter 141 and is configured to change an irradiation range of the near-infrared rays on the tooth T with which the tooth T is irradiated. It is sufficient for the variable focal length lens 142 to have an optical configuration capable of changing a focal length, and may be a single optical element such as a liquid lens, or may be configured by a plurality of optical elements such as a lens unit that can change a focal length by changing an interval between two or more lenses. In the embodiment, the variable focal length lens 142 will be described as a mode to which the liquid lens is applied.

The optical system 14 may further include other optical equipment, such as an optical fiber and various mirrors, in order to form the above-described paths of light.

Here, the light source 11, the transmitted light detection sensor 12, and the optical system 14 constitute an optical system that irradiates the tooth T with near-infrared rays from the light source 11 and detects the transmitted light through the tooth T. The optical system in the embodiment is also referred to as a screening optical system 10A. In the embodiment, the screening optical system 10A further includes the variable focal length lens 142, more specifically, for example, a liquid lens, as a variable focal length optical system capable of changing the irradiation range of the near-infrared rays on the tooth T.

In addition, the light source 11, the Raman scattered light detection sensor 13, and the optical system 14 constitute an optical system that irradiates a caries candidate area of the tooth T, which will be described later, with near-infrared rays from the light source 11 and detects Raman scattered light generated from the caries candidate area. The optical system in the embodiment is also referred to as a Raman scattered light detection optical system 10B. In the embodiment, the Raman scattered light detector optical system 10B further includes the optical filter 141 that transmits only light of a specific wavelength from the Raman scattered light generated from the caries candidate area.

The display device 15 is a device configured to display one or both of an image based on information of the transmitted light detected by the screening optical system 10A and an image based on information of the Raman scattered light detected by the Raman scattered light detection optical system 10B. It is sufficient for an "image based on information of detected light" to be an image that can be visually recognized as the information by a user of the caries detection device, and examples thereof include an image of the tooth T, a spectrum and a graph indicating a characteristic (intensity, wavelength, or the like) of the detected light. The display device 15 is a device that visually outputs the above information, and is, for example, a liquid crystal display.

In the embodiment, the light source 11 is a device that outputs near-infrared rays in both the screening optical system 10A and the Raman scattered light detection optical system 10B. That is, both first inspection light in the screening optical system 10A and second inspection light in the Raman scattered light detection optical system 101 are the near-infrared rays in the embodiment.

In the embodiment, the light source 11, the transmitted light detection sensor 12, the Raman scattered light detection sensor 13, and the optical system 14 are held by an inspection jig so as to be capable of inspecting the tooth T of an oral cavity. The inspection jig is an instrument that can be inserted into a human oral cavity, and holds at least the transmitted light detection sensor 12 and the variable focal length lens 142 so as to be capable of inspecting the tooth T of the oral cavity, for example. In the embodiment, the inspection jig holds the transmitted light detection sensor 12 on the back side of the oral cavity, and holds the light source 11, the optical system 14, and the Raman scattered light detection sensor 13 on the front side of the oral cavity with the tooth T interposed therebetween.

[Functional Configuration]

FIG. 2 is a block diagram illustrating an example of a functional configuration of the caries detection device according to the embodiment. The caries detection device 1 further includes a control unit 16. The control unit 16 is, for example, a processor, and implements desired control by a program configured to function as a specific control block. As illustrated in FIG. 2, the control unit 16 includes a caries candidate area identification unit 161, which identifies a caries candidate area, a caries detection unit 162, a focal length control unit 163, a display control unit 164, a second inspection light irradiation position correction unit 165, a shake correction unit 166, and a difference detection unit 167.

[Caries Detection]

The caries detection using the caries detection device 1 may be performed by a user, such as a dentist, manually operating the caries detection device 1, or may be partially or entirely performed automatically by a control device. Hereinafter, a mode of using control by the control device will be described as an example of the caries detection using the caries detection device 1 in the embodiment. FIG. 3 is a flowchart illustrating an example of a caries detection process according to the embodiment.

<Screening>

The caries candidate area identification unit 161 starts measurement of screening of caries of the tooth T of a subject (step S301). The screening is performed by irradiating the tooth T with near-infrared rays. The control unit 16 causes the light source 11 to generate the near-infrared rays. The near-infrared rays generated by the light source 11 are reflected by the optical filter 141, and are emitted to the tooth T through the variable focal length lens 142 which is the liquid lens.

Figure 4:
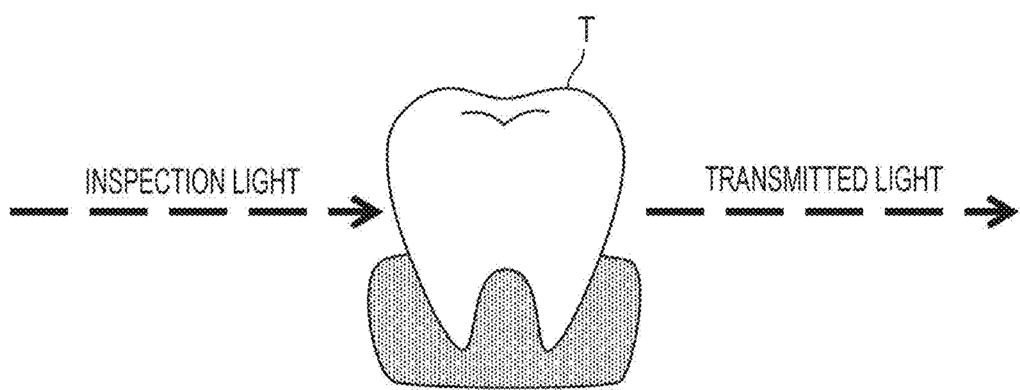
FIG. 4 is a view for describing screening of a caries candidate area according to the first embodiment of the invention.

FIG. 4 is a view for describing the screening of a caries candidate area in the embodiment. The near-infrared rays penetrate the enamel and dentin of the tooth T. Accordingly, the transmitted light detection sensor 12 receives and detects transmitted light of the near-infrared rays.

For example, when all the teeth T of the subject are sequentially irradiated with the near-infrared rays in this manner, information of the transmitted light of the near-infrared rays of all the teeth T of the subject is obtained as an image of the transmitted light through the teeth T in this manner, the caries candidate area identification unit 161 acquires an image of the near-infrared rays transmitted through the teeth T as a screening image (step S302).

Figure 5:
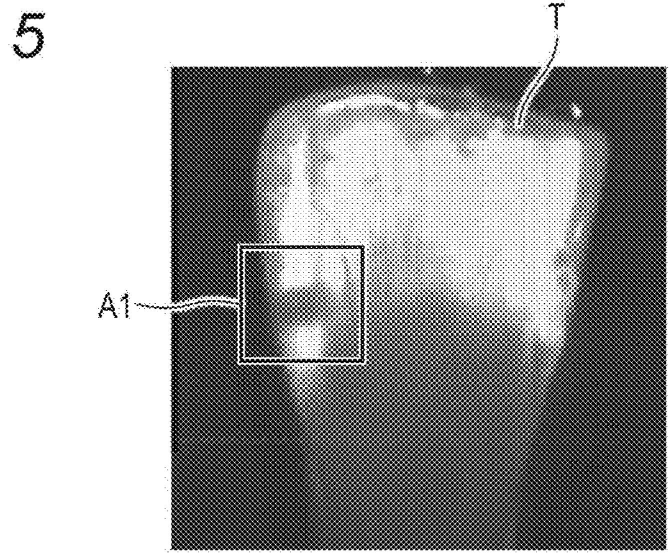
FIG. 5 is a view illustrating a photograph showing an example of an image illustrating the caries candidate area obtained by screening according to the first embodiment of the invention.

Next, the caries candidate area identification unit 161 analyzes the image (step S303). FIG. 5 is a view illustrating a photograph showing an example of an image illustrating the caries candidate area obtained by the screening in the embodiment. Note that the photograph illustrated in FIG. 5 is cited from Graham C. Jones, Robert. S. Jones and Daniel Fried, Proc. of SPIE, 5313, 17 (2004).

In the normal tooth T without caries, near-infrared rays pass through the enamel or dentin. On the other hand, the near-infrared rays are absorbed, reflected, or scattered at a singular portion in the tooth T in which the singular portion of a cavity, deterioration, or the like exists in the enamel or dentine, such as caries. Therefore, an area of the tooth T suspected of having the caries (caries candidate area) is represented as a dark portion in the image of the transmitted light of the near-infrared rays through the tooth T as illustrated in a frame A1 of FIG. 5. Accordingly, the dark portion as in the photograph shown in FIG. 5 can be determined as the caries candidate area. The caries candidate area identification unit 161 identifies the caries candidate area according to information of the transmitted light, detected by the screening optical system 10A, by determining the presence or absence of such a difference in brightness on the basis of a predetermined threshold, for example.

<Caries Detection by Raman Scattering>

Figure 6:
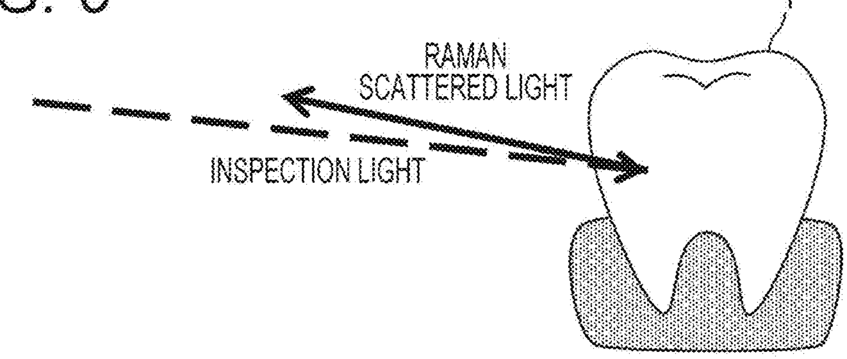
FIG. 6 is a view for describing detection of a caries according to the first embodiment of the invention.

Next, the caries detection unit 162 starts Raman spectroscopy, measurement (step S304). FIG. 6 is a view for describing the caries detection according to the embodiment. First, the focal length control unit 163 controls a voltage applied to the liquid lens as the variable focal length lens 142 to focus near-infrared rays from the light source 11 to a caries candidate area determined by the caries candidate area identification unit 161 on the specific tooth T. The caries candidate area is, for example, the dark portion in the frame A1 of FIG. 5. In this manner, the caries detection unit 162 focuses the near-infrared rays on the caries candidate area and starts the Raman spectroscopy measurement.

Next, the caries detection unit 162 obtains a Raman spectrum (step S305). The caries candidate area is a very small area of the tooth T, and the near-infrared rays from the light source 11 are intensively emitted to the caries candidate area. The light including the Raman scattered light generated in the caries candidate area reaches the optical filter 141. Out of the light, only Raman scattered light passes through the optical filter 141. Accordingly, a part of the Raman scattered light generated in the caries candidate area reaches the Raman scattered light detection sensor 13 via the optical system 14 and is detected. The intensity of Raman scattered light is usually weak, but the Raman spectrum of the caries candidate area is obtained in a short period of time since the near-infrared rays as the inspection light are intensively emitted to the caries candidate area.

Figure 7:
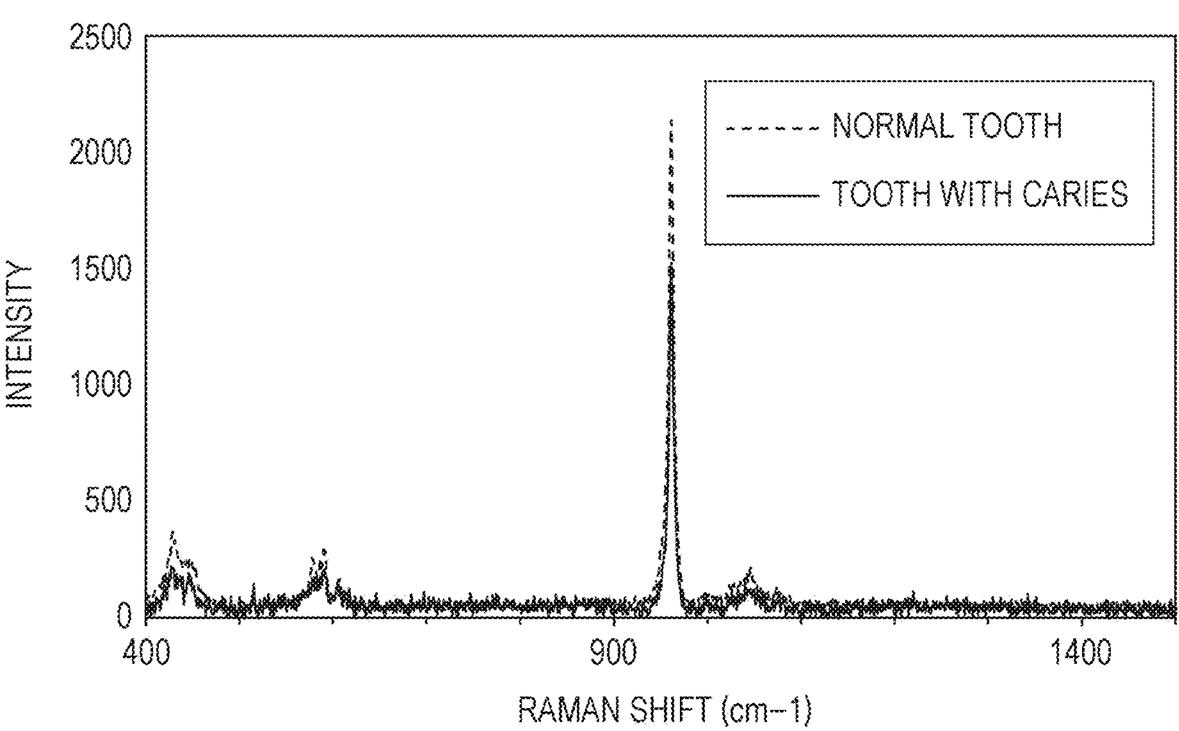
FIG. 7 is a view illustrating an example of a caries detection result according to the first embodiment of the invention.

Next, the caries detection unit 162 analyzes the Raman spectrum (step S306). FIG. 7 is a view illustrating an example of a caries detection result in the embodiment. As illustrated in FIG. 7, the Raman scattered light generated from the tooth T has a peak at the same position between 900 to 1000 $cm^{-1}$, but the intensity of the Raman scattered light is clearly lower in an area of the caries in the tooth T than in a normal area of the tooth T. The caries detection unit 162 analyzes the Raman spectrum for each caries candidate area by, for example, superimposing individual Raman spectra or comparing specific peak intensities or an intensity ratio between a plurality of peaks as illustrated in FIG. 7.

Next, the caries detection unit 162 performs caries diagnoses (step S307). The caries detection unit 162 determines a caries candidate area, which satisfies a specific requirement in the Raman spectrum among the caries candidate areas, as caries. For example, the caries detection unit 162 determines whether or not there is caries on the basis of a predetermined threshold of the peak intensity. Alternatively, the caries detection unit 162 calculates a difference (or ratio) between the intensity of the Raman scattered light in the caries candidate area and the intensity of the Raman scattered light in the normal area, and determines whether or not there is caries on the basis of a threshold determined in advance for the difference or the ratio. In this manner, the degree of caries of the caries candidate area is evaluated according to the information of the Raman scattered light detected by the Raman scattered light detection optical system 103.

<Prevention of Erroneous Diagnosis>

It is difficult to continuously and completely stop a movement of the subject such as a patient or the user such as a dentist in caries detection work. Accordingly, there is a possibility that an area where Raman spectroscopy measurement is performed does not coincide with the caries candidate area in the screening image. In order to prevent erroneous diagnosis caused by such inconsistency, the screening may be performed after the detection of Raman scattered light in the embodiment. For example, in the embodiment, the process may return to the acquisition of the screening image in step S302 after the acquisition of the Raman spectrum (step S305) is measured a certain number of times as indicated by a broken line arrow in FIG. 3. Further, the image analysis in step S303 may be performed as necessary to determine whether or not the position of the measurement of the Raman scattering needs to be corrected. Alternatively, the transition to step S302 may be performed after a lapse of a certain period of time since the acquisition of the Raman spectrum.

The control unit 16 performs control for preventing the erroneous diagnosis as necessary at the time of caries detection (diagnosis). In a case where the user such as a dentist diagnoses caries, the display control unit 164 displays, on the display device 15, an image of a specific caries candidate area based on information of the transmitted light detected by the screening optical system 10A and an image of the specific caries candidate area based on information of the Raman scattered light detected by the Raman scattered light detection optical system 10B. The control unit 16 obtains the "image of the specific caries candidate area based on the information of the transmitted light detected by the screening optical system 10A" referred to herein by obtaining the image of the Raman scattered light of the specific caries candidate area by the Raman scattered light detection optical system 10B, and then, performing imaging again.

The control unit 16 automatically performs this image display on the display device 15 in response to, for example, an input signal from the user or in association with the caries diagnosis in step S307 described above. The display control unit 164 displays the above two images side by side on one screen on the display device 15, or displays the images in an overlapping manner as the images of the same scale. According to such processing, it is possible to refer to a measurement position in Raman spectroscopy measurement after the Raman spectroscopy measurement of the caries candidate area, and a position on a tooth T where the inspection light is focused is confirmed on the basis of the screening image captured after the Raman spectroscopy measurement. As a result, even if a position different from an assumed position has been measured, the user can easily notice such an error in the measurement position, and erroneous diagnosis caused by the error in the measurement position can be prevented.

<Suppression of Measurement Error>

It is difficult to completely stop the movement of the subject and the user in the caries detection as described above. Accordingly, the control unit 16 may further perform control to suppress a measurement error at the time of detecting the transmitted light or at the time of detecting the Raman scattered light in the screening.

For example, the second inspection light irradiation position correction unit 165 corrects a deviation of an irradiation position of a near-infrared ray in a caries candidate area according to information of the caries candidate area. The correction of the deviation of the irradiation position can be implemented, for example, as the caries detection device 1 transmits a first signal indicating that the irradiation position maintains an original irradiation position, and then, the caries detection device 1 transmits a second signal indicating that the irradiation position deviates from the original position.

Both the first signal and the second signal may be visible signals such as images displayed on the display device 15, or may be signals in a form that is not displayed on a screen such as sound. The second signal may change depending on the magnitude of the deviation from the original position. Such control is advantageous from the viewpoint that a position where near-infrared rays are focused is appropriately corrected at any time during the Raman spectroscopy measurement and the focus position of the near-infrared rays is made fixed. Accordingly, an effect of the movement of the user performing the measurement (for example, shaking of a hand) on a measurement result is suppressed.

In addition, for example, the shake correction unit 166 cancels an effect of shakes of the screening optical system and the Raman scattered light detection optical system on a tooth. Such control is implemented, for example, by detecting the shake caused by shaking of the above-described inspection jig and moving an optical path of near-infrared rays in a direction in which the shake is canceled in accordance with the shake. The control can be performed in the same manner as a shake prevention function in an optical device such as a camera and a telescope. The control is also advantageous from the viewpoint of suppressing the effect of the movement of the user performing the measurement (for example, shaking of a hand) on the measurement result.

In addition, for example, the difference detection unit 167 detects a difference in position between an image of a specific caries candidate area based on information of the transmitted light detected by the screening optical system 10A and an image of the specific caries candidate area based on information of the Raman scattered light detected by the Raman scattered light detection optical system 10B. Such a difference in position can be detected using a known method such as an inter-frame difference method and a background difference method. More specifically, it is possible to obtain how far a movement has been made (that is, the difference in position) by combining difference images before and after the movement with a method of determining a position such as triangulation. According to the control, the user can confirm a positional deviation, the user can recognize a cause of the positional deviation from a direction, a timing, and the like of the positional deviation, and the user can pay attention to the movement that has led to the cause. The control is also advantageous from the viewpoint of removing the effect of the movement of the user performing the measurement (for example, shaking of a hand).

Main Functions and Effects of Embodiment

As the lifespan of human beings is extending worldwide, an extension of a health span, which is a period during which one can live without nursing care, has become an important social problem. It has been found that elderly people with a large number of teeth tend to have a long health span as results of research and studies so far. Periodontal diseases, such as “caries” and “periodontitis”, account for a large proportion as a factor of losing tooth. Therefore, how to prevent or detect the periodontal diseases at an early stage is important.

When attention is paid to “caries”, which is one of the periodontal diseases, the “caries” has been detected by a radiography device or palpation by a dentist. However, it is difficult to detect the “caries” at an early stage in the radiography device, which is substantially the only inspection device in widespread use, and the caries is often at a stage of requiring scraping already even if being detected.

In addition, the palpation by the dentist greatly depends on his/her own experience, and it is difficult to avoid a problem of erroneous diagnosis. In recent years, it has been revealed that the “caries” at the early stage can be treated without scraping a tooth, and a concept of preventive dentistry that prevents progress of the “caries” has attracted great attention. As described above, a technique of accurately detecting the early “caries” has attracted attention and been desired in recent years.

A carious portion of a tooth can be detected by Raman spectroscopy with high accuracy, and is advantageous from the viewpoint of detecting the “caries” at the early stage. On the other hand, the intensity of the Raman scattered light generated by irradiation of the tooth with the inspection light is weak, and thus, a measurement time of the Raman spectroscopy becomes long. Normal teeth occupy a much larger surface area than the carious portion, and it should be said that the Raman spectroscopy is unsuitable from the viewpoint of an appropriate measurement time to detect the caries from the entire tooth which is a wider space range than the carious portion.

In the embodiment, candidate areas of caries of the tooth T are detected on the basis of image information of the transmitted light through the tooth T generated by the near-infrared rays, and caries of the tooth T is detected by detecting the Raman scattered light caused by the near-infrared rays for each of the detected caries candidate areas. It is possible to selectively measure only a site suspected of the “caries” by the Raman spectroscopy by combining the screening technique using the near-infrared rays capable of measuring a wide range and the Raman spectroscopy in the embodiment. Thus, a measurement time is shortened as compared with the case where the caries is detected only by the Raman spectroscopy. Accordingly, it is possible to quickly and accurately detect the early caries in the embodiment.

In addition, the inspection light is the near-infrared rays in both the screening optical system 10A and the Raman scattered light detection optical system 10B in the embodiment. Accordingly, light generated from the light source 11 is only the near-infrared rays, and thus, the configuration of the light source 11 can be simplified. In addition, there is the single inspection light, it is sufficient for the Raman scattered light that needs to be detected to be separable from the single inspection light (near-infrared rays), which is advantageous from the viewpoint of simplifying the configuration of the Raman scattered light detection optical system 10B.

In addition, the screening optical system 10A further includes the variable focal length lens 142, for example, a liquid lens, as the variable focal length optical system in the embodiment. As a result, it is possible to easily change the irradiation range of the inspection light from the entire tooth T to the caries candidate area. Accordingly, it is advantageous from the viewpoint of performing the screening of the caries candidate area to the caries detection by the same device.

In the embodiment, the Raman scattered light detection optical system 10B further includes the optical filter 141. Since the optical filter 141 can transmit only light of a specific wavelength, such as a component generated from the caries candidate area, out of the Raman scattered light, it is possible to detect only an effective wavelength or detect a component of light of a different specific wavelength and easily obtain an intensity ratio therebetween. Thus, the time required for the caries detection can be further shortened.

In addition, the caries detection device 1 further includes the display device 15 in the embodiment. Accordingly, it is advantageous from the viewpoint of using the image of the transmitted light through the tooth T in the screening in the caries detection by the Raman spectroscopy.

In addition, it is necessary to fix a site suspected of the caries and focus light when caries is diagnosed by Raman spectroscopy, but it is practically difficult to completely fix a movement of a patient and a movement of a hand of a dentist. Therefore, the possibility that erroneous diagnosis is made by assuming a site actually having no caries as a carious site and measuring the site is sufficiently conceivable. Since various systems for correcting the measurement position can be introduced in the embodiment, the possibility of such erroneous diagnosis can be further reduced.

Second Embodiment

Another embodiment of the invention will be described hereinafter. For convenience of the description, members having the same functions as the members described in the above embodiment will be denoted by the same reference signs, and the description thereof will not be repeated.

[Configuration of Device]

Figure 8:
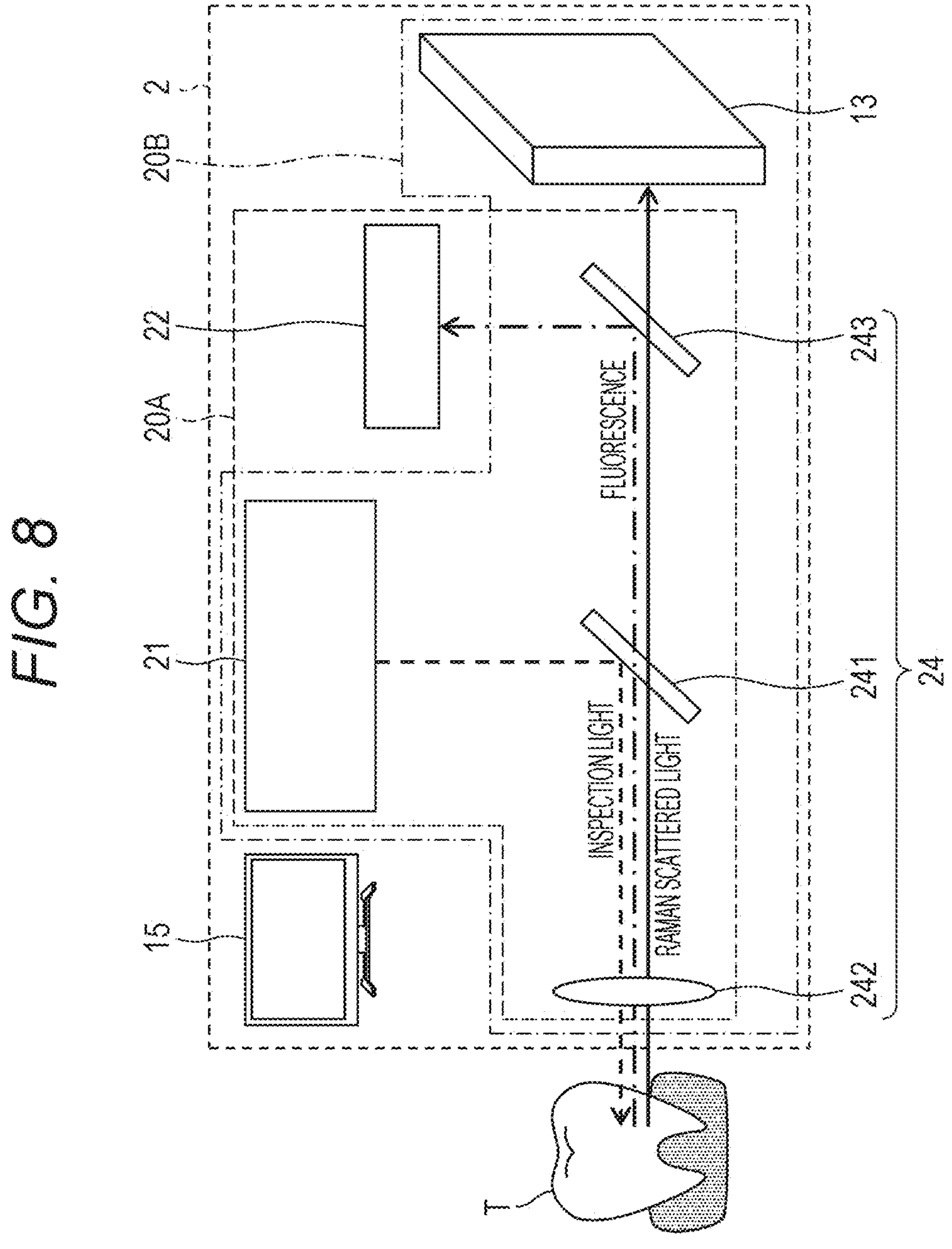
FIG. 8 is a diagram schematically illustrating a configuration of a caries detection device according to a second embodiment of the invention.

FIG. 8 is a diagram schematically illustrating a configuration of a caries detection device according to this embodiment. As illustrated in FIG. 8, a caries detection device 2 includes a screening optical system 20A and a Raman scattered light detection optical system 20B. The screening optical system 20A includes a light source 21, a fluorescence detection sensor 22, and optical system 24. The screening optical system 20A is an optical system that irradiates the tooth T with excitation light that is first inspection light from the light source 21 and detects fluorescence generated from the tooth T. The Raman scattered light detection optical system 20B includes the light source 21, the Raman scattered light detection sensor 13, and the optical system 24. The Raman scattered light detection optical system 20B is an optical system that irradiates a caries candidate area of the tooth T detected from information of the fluorescence with a near-infrared ray, which is second inspection light from the light source 21, and detects Raman scattered light generated from the caries candidate area.

In the embodiment, the fluorescence is fluorescence generated by the tooth T irradiated with the excitation light that is the first inspection light. It is sufficient for the excitation light to be any light that causes excitation peculiar to caries in a tooth with the caries and generates fluorescence peculiar to the caries. As the excitation light, visible light having a partial wavelength in a wavelength range of 300 to 800 nm can be applied.

The light source 21 is a device that generates excitation light and a near-infrared ray. The excitation light is inspection light for screening, and is light that generates fluorescence from a tooth with caries. The excitation light is light having a shorter wavelength than the fluorescence, and is, for example, visible light including a part of a wavelength selected from the wavelength range of 300 to 800 nm. The near-infrared ray is inspection light for detection of Raman scattered light, and is light that generates Raman scattered light from a caries candidate area. As the light source 21, a high-output light source, such as a semiconductor laser and a fiber laser, is used. The light source 21 may be a wavelength-tunable light source, or may be a plurality of light sources respectively corresponding to the excitation light and the near-infrared ray.

The fluorescence detection sensor 22 is a sensor configured to detect the fluorescence generated when the tooth T is irradiated with the excitation light that is the first inspection light. As the fluorescence detection sensor 22, an image sensor, such as a CMOS camera and a CCD camera, can be used. For example, the CMOS camera is used in the embodiment.

The optical system 24 includes optical filters 241 and 243 and a variable focal length lens 242.

The optical filter 241 is disposed between the light source 21 and the tooth T, reflects the excitation light from the light source 21 toward the tooth T, and transmits the other light. As the optical filter 241, a band-pass filter, an edge filter, a long-pass filter, a dichroic mirror, a notch filter, or the like can be used. In the embodiment, the optical filter 241 is, for example, the notch filter, the edge filter, the dichroic mirror, or the long-pass filter.

The variable focal length lens 242 is disposed between the optical filter 241 and the tooth T, and is disposed on an optical path of the inspection light from the optical filter 241 and the fluorescence or the Raman scattered light from the tooth T. The variable focal length lens 242 can focus at least the inspection light from the optical filter 241 on the surface of the tooth T. In the embodiment, the variable focal length lens 242 has an optical configuration capable of changing a focal length, which is similar to the variable focal length lens 142, and is, for example, a liquid lens.

The optical filter 243 is disposed between the optical filter 241, and the fluorescence detection sensor 22 and the Raman scattered light detection sensor 13 on a side opposite to the variable focal length lens 242 with respect to the optical filter 241. The optical filter 243 reflects the fluorescence from the tooth T toward the fluorescence detection sensor 22 and transmits the other light. In the embodiment, the optical filter 243 is, for example, an edge filter, a dichroic mirror, or a long-pass filter.

Note that a functional configuration in the embodiment is substantially the same as the configuration illustrated in FIG. 2 except that the fluorescence detection sensor 22 is connected to the control unit 16, instead of the transmitted light detection sensor 12.

[Caries Detection]

Caries detection using the caries detection device 2 can be performed substantially in the same manner as that of the first embodiment described above except for screening.

<Screening>

Figure 9:
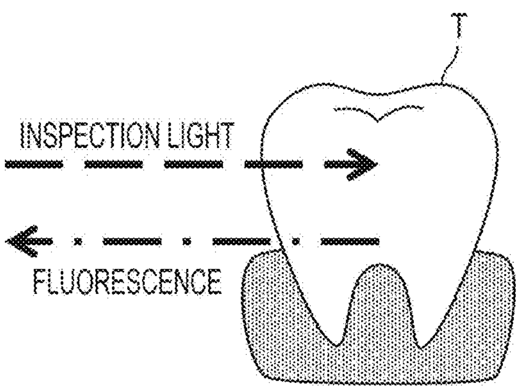
FIG. 9 is a view for describing screening of a caries candidate area according to the second embodiment of the invention.
Figure 10:
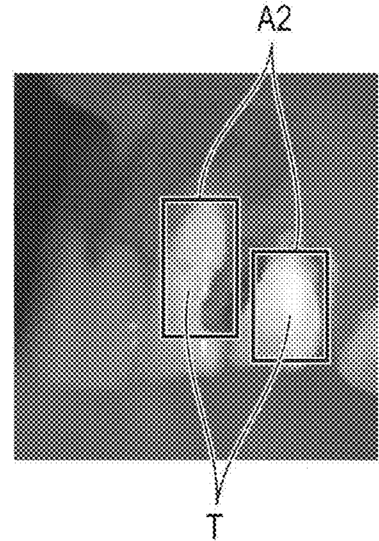
FIG. 10 is a view illustrating a photograph showing an example of an image illustrating the caries candidate area obtained by screening according to the second embodiment of the invention.

The control unit 16 causes the light source 21 to generate the excitation light. The excitation light generated by the light source 21 is reflected by the optical filter 241 and emitted to the tooth T through the variable focal length lens 242 (liquid lens). FIG. 9 is a view for describing screening of a caries candidate area in the embodiment. The excitation light is reflected or scattered by the normal tooth T. On the other hand, regarding the tooth T with caries, the excitation light is absorbed by a carious portion and generates fluorescence having a longer wavelength as illustrated in FIG. 9. For example, when the tooth T with caries is irradiated with the excitation light, red fluorescence is generated as indicated by a frame A2 in FIG. 10. FIG. 10 is a view illustrating a photograph showing an example of an image illustrating the caries candidate area obtained by the screening in the embodiment. Note that the photograph illustrated in FIG. 10 is cited from Tokuji HASEGAWA, Dental Medicine Research, 33, 259-264 (2013).

The fluorescence passes through the variable focal length lens 242, passes through the optical filter 241, is reflected by the optical filter 243 toward the fluorescence detection sensor 22, is received by the fluorescence detection sensor 22, and is detected. In the embodiment, the caries candidate area identification unit 161 identifies a caries candidate area according to information of the fluorescence, detected by the screening optical system 20A, by determining the presence or absence of such fluorescence on the basis of a predetermined threshold, for example.

<Others>

In the embodiment, caries detection using Raman spectroscopy is performed in the same manner as in the first embodiment described above except that the inspection light generated by the light source 21 is switched from excitation light to a near-infrared ray. In addition, control for preventing erroneous diagnosis and suppressing a measurement error in the embodiment can be performed in the same manner as in the first embodiment.

Main Functions and Effects of Embodiment

In the embodiment, caries candidate areas of the tooth T are detected on the basis of image information of the fluorescence of the tooth T obtained by irradiation with the excitation light, and caries of the tooth T is detected by detecting the Raman scattered light by the near-infrared ray for each of the detected caries candidate areas. In the embodiment, the tooth T is screened by the fluorescence peculiar to the caries of the tooth T, and thus, it is possible to quickly and accurately detect early caries as in the first embodiment described above.

In the embodiment, the inspection light in the screening is the light that generates the fluorescence peculiar to the caries from the tooth with the caries, for example, light having a shorter wavelength than the fluorescence, and the inspection light in the detection of Raman scattered light is the near-infrared ray. In the embodiment, fluorescence generated in a direction opposite to a traveling direction of the inspection light can be focused and detected out of the above fluorescence. Accordingly, both the screening optical system 20A and the Raman scattered light detection optical system 20B are disposed on the front side of an oral cavity of a subject with respect to the tooth T. Therefore, the tooth T is irradiated with the inspection light from the front side of the oral cavity, and detection light is detected on the front side. Thus, it is possible to more easily detect a caries candidate area and caries in the oral cavity of the subject such as a patient.

Other Embodiments

The invention is not limited to the above-described embodiments, and various modifications can be made within the scope indicated in the claims. Embodiments obtained by appropriately combining technical means disclosed in different embodiments are also included in the technical scope of the invention.

For example, the display device 15 may also serve as an input device for a user in the embodiment of the invention. For example, the display device 15 may further include a touch panel.

In addition, a caries candidate area and a carious portion may be determined by a user such as a dentist in the embodiment of the invention. In a case where the user determines the caries candidate area, the subsequent detection of Raman scattered light may be automatically performed as the user inputs a determination result. Alternatively, the user may manually perform Raman spectroscopy analysis on an automatically determined caries candidate area, and make a final determination on caries detection on the basis of the result thereof.

In addition, the program for causing the control unit 16 to implement desired control may be supplied to the control unit 16 via an arbitrary wired or wireless transmission medium in the embodiment of the invention. In addition, some or all of the functions of the control blocks in the control unit 16 can also be implemented by logic circuits. The control unit 16 may be, for example, an integrated circuit in which the logic circuits functioning as the respective control blocks described above are formed. In addition, for example, the functions of the control blocks can be implemented by a quantum computer.

In addition, each processing described in the embodiment of the invention may be executed by artificial intelligence (AI). For example, the AI may be caused to execute the determination of a caries candidate area, the determination of a carious portion, or the diagnosis of caries in the embodiment of the invention. JP 2018-521701 A described above proposes a calculation formula for quantitatively evaluating the degree of progress of caries from a Raman spectrum of a tooth. On the basis of knowledge of such quantitative evaluation, it is expected that sufficiently useful results for the caries candidate area, the carious portion, and the diagnosis thereof can be obtained by the AI. The AI may operate in the control unit, or may operate in another device (for example, an edge computer, a cloud server, or the like) in the embodiment of the invention.

Summary

As apparent from the above description, a caries detection device (1 or 2) according to the embodiment of the invention includes: a screening optical system (10A or 20A) that irradiates a tooth (T) with first inspection light from a light source (11 or 21) and detects transmitted light through the tooth or fluorescence generated from the tooth; and a Raman scattered light detection optical system (10B or 20B) that irradiates a caries candidate area, which is identified from information of the transmitted light or the fluorescence detected by the screening optical system, in the tooth with second inspection light from the light source and detects Raman scattered light generated from the caries candidate area. Accordingly, the caries detection device can detect caries by the detection of the Raman scattered light in a shorter period of time as compared with a case where screening and caries detection are performed by Raman spectroscopy.

The caries detection device according to the embodiment of the invention may further include a caries candidate area identification unit that identifies the caries candidate area in accordance with information of the transmitted light or the fluorescence detected by the screening optical system. This configuration is even more effective from the viewpoint of quickly determining the caries candidate area, and implementing the caries detection in a short period of time.

In addition, the caries detection device according to the embodiment of the invention may further include a caries detection unit that detects caries in the caries candidate area in accordance with information of the Raman scattered light detected by the Raman scattered light detection optical system. This configuration is even more effective from the viewpoint of implementing the caries detection in a short period of time.

In addition, the first inspection light and the second inspection light may be both near-infrared rays in the embodiment of the invention. This configuration is even more effective from the viewpoint of simplifying the configuration of the caries detection device since it is sufficient for the light source to be a device that Generates single light (near-infrared ray).

Alternatively, in the embodiment of the invention, the first inspection light may be light having a shorter wavelength than the fluorescence (excitation light), and the second inspection light may be a near-infrared ray. This configuration is even more effective from the viewpoint of facilitating the operation of detecting the caries since it is possible to configure the caries detection device capable of detecting the caries candidate area and the caries from a front side of an oral cavity with respect to a tooth to be detected.

In the embodiment of the invention, the screening optical system may further include a variable focal length optical system capable of changing an irradiation range of the first inspection light on the tooth. This configuration is more effective from the viewpoint or constructing a simple optical system capable of detecting both the caries candidate area and the caries.

Furthermore, the variable focal length optical system may further include a liquid lens in the embodiment of the invention. This configuration is even more effective from the viewpoint of constructing a simple optical system capable of detecting both the caries candidate area and the caries.

In addition, the caries detection device according to the embodiment of the invention may further include a second inspection light irradiation position correction unit that corrects a deviation of an irradiation position of the second inspection light in the caries candidate area in accordance with information of the caries candidate area. This configuration makes it possible to correct a position where the inspection light is collected at the time of Raman spectroscopy measurement at any time to make a light focus position constant, and thus, it is even more effective from the viewpoint of suppressing an effect of a movement (for example, shaking of a hand) of a user such as a dentist who performs the measurement on a detection result.

In addition, the caries detection device according to the embodiment of the invention may further include a shake correction unit that cancels an effect of shakes of the screening optical system and the Raman scattered light detection optical system on the tooth. This configuration is even more effective from the viewpoint of suppressing the effect of shaking of the user at the time of detecting the caries candidate area and the caries on the detection result.

In the embodiment of the invention, the Raman scattered light detection optical system may further include a filter that transmits only light of a specific wavelength from the Raman scattered light generated from the caries candidate area. This configuration makes it possible to detect an intensity ratio between a component of the light having the specific wavelength and a component of light having a different wavelength, which is even more effective from the viewpoint of implementing the caries detection in a short period of time.

In addition, the caries detection device according to the embodiment of the invention may further include a display device (15) that displays one or both of an image based on information of the transmitted light or the fluorescence detected by the screening optical system and an image based on the information of the Raman scattered light detected by the Raman scattered light detection optical system. This configuration is even more effective from the viewpoint of enabling the caries detection using the images acquired at the time of detecting the caries candidate area and the caries and enhancing the accuracy of the caries detection.

In addition, the caries detection device according to the embodiment of the invention may further include a display control unit that displays, on the display device, an image of a specific caries candidate area based on information of the transmitted light or the fluorescence detected by the screening optical system and an image of the specific caries candidate area based on information of the Raman scattered light detected by the Raman scattered light detection optical system. This configuration makes it possible to easily confirm each detected site using the images acquired at the time of detecting the caries candidate area and the caries, which is even more effective from the viewpoint of preventing erroneous caries detection.

In addition, the caries detection device according to the embodiment of the invention may further include a difference detection unit that detects a difference in position between the image of the specific caries candidate area based on the information of the transmitted light or the fluorescence detected by the screening optical system and the image of the specific caries candidate area based on the information of the Raman scattered light detected by the Raman scattered light detection optical system. With this configuration, it is possible to easily confirm whether a detection position of the caries candidate area and a detection position of the caries based on the caries candidate area are correct or incorrect after the caries detection. Accordingly, it is even more effective from the viewpoint of preventing the erroneous caries detection.

According to the above-described configuration in the embodiment of the invention, it is possible to accurately, quickly, and easily detect a periodontal disease such as the caries at an early stage. Accordingly, it is expected that the early detection of the periodontal disease will lead to an extension of a health span, and will contribute to ensuring a healthy life of people in sustainable development goals (SDGs) according to the embodiment of the invention.

What is claimed is:

1. A caries detection device comprising:

a fluorescence detection sensor configured to detect fluorescence generated from a tooth;

a screening optical system that irradiates the tooth with first inspection light from a light source and detects transmitted light through the tooth or fluorescence generated from the tooth to identify a caries candidate area; and a Raman scattered light detection optical system that irradiates the caries candidate area, which is identified from information of an image generated from the transmitted light or the fluorescence detected by the screening optical system, in the tooth with second inspection light from the light source and detects Raman scattered light generated from the caries candidate area, wherein a part of the screening optical system and a part of the Raman scattered light detection optical system are configured by a common optical system, and wherein the common optical system forms a path in which the fluorescence passes through a variable focal length lens and an optical filter, and is reflected by the optical filter toward the fluorescence detection sensor to identify the caries candidate area.

2. The caries detection device according to claim 1, further comprising circuitry configured to identify the caries candidate area in accordance with information of the transmitted light or the fluorescence detected by the screening optical system.

3. The caries detection device according to claim 1, further comprising circuitry configured to detect caries of the caries candidate area in accordance with information of an image generated from the Raman scattered light detected by the Raman scattered light detection optical system.

4. The caries detection device according to claim 1, wherein the first inspection light and the second inspection light are both near-infrared rays.

5. The caries detection device according to claim 1, wherein the first inspection light is light having a shorter wavelength than the fluorescence, and the second inspection light is a near-infrared ray.

6. The caries detection device according to claim 1, wherein the screening optical system further includes a variable focal length optical system capable of changing an irradiation range of the first inspection light on the tooth.

7. The caries detection device according to claim 6, wherein the variable focal length optical system further includes a liquid lens.

8. The caries detection device according to claim 1, further comprising circuitry further configured to correct a deviation of an irradiation position of the second inspection light in the caries candidate area in accordance with information of the caries candidate area.

9. The caries detection device according to claim 1, further comprising circuitry configured to cancel an effect of shakes of the screening optical system and the Raman scattered light detection optical system on the tooth.

10. The caries detection device according to claim 1, wherein the Raman scattered light detection optical system further includes a filter that transmits only light of a specific wavelength from the Raman scattered light generated from the caries candidate area.

11. The caries detection device according to claim 1, further comprising a display device that displays one or both of an image based on information of the transmitted light or the fluorescence detected by the screening optical system and an image based on information of the Raman scattered light detected by the Raman scattered light detection optical system.

12. The caries detection device according to claim 11, further comprising circuitry further configured to control a display of, on the display device, an image of a specific caries candidate area based on information of the transmitted light or the fluorescence detected by the screening optical system and an image of the specific caries candidate area based on information of the Raman scattered light detected by the Raman scattered light detection optical system.

13. The caries detection device according to claim 12, wherein the circuitry is further configured to detect a difference in position between the image of the specific caries candidate area based on the information of the image generated from the transmitted light or the fluorescence detected by the screening optical system and the image of the specific caries candidate area based on the information of the image generated from the Raman scattered light detected by the Raman scattered light detection optical system.

* * * * *